United States Patent [19]

Dechene et al.

[11] Patent Number: 5,054,325
[45] Date of Patent: Oct. 8, 1991

[54] FLOW MEASUREMENT BY COLLISION CHARACTERIZATION

[75] Inventors: Ronald L. Dechene, Boxford, Mass.; Thomas B. Smith, Atkinson, N.H.; Robert E. Newton, Tewksbury, Mass.

[73] Assignee: Auburn International, Inc., Danvers, Mass.

[21] Appl. No.: 475,722

[22] Filed: Feb. 5, 1990

[51] Int. Cl.⁵ .............................................. G01F 1/56
[52] U.S. Cl. .............................. 73/861.04; 73/861.08; 324/454
[58] Field of Search ............ 73/861.04, 861.08, 861.09; 324/71.4, 454, 464

[56] References Cited

U.S. PATENT DOCUMENTS

| | | | |
|---|---|---|---|
| 3,906,780 | 9/1975 | Baldwin | 73/861.04 X |
| 4,531,486 | 7/1985 | Reif et al. | 324/464 X |
| 4,904,944 | 2/1990 | Dechene et al. | 73/861.08 X |

*Primary Examiner*—Herbert Goldstein
*Attorney, Agent, or Firm*—Jerry Cohen; Edwin H. Paul

[57] ABSTRACT

Particle analysis apparatus (10) in combination with a triboelectric probe (P) and including means (18, 20, 22, 24, 26) to analyze individual particle collisions with the probe as a useful measure of flow conditions—of a fluid with suspended solid particles—in the region of the probe.

4 Claims, 1 Drawing Sheet

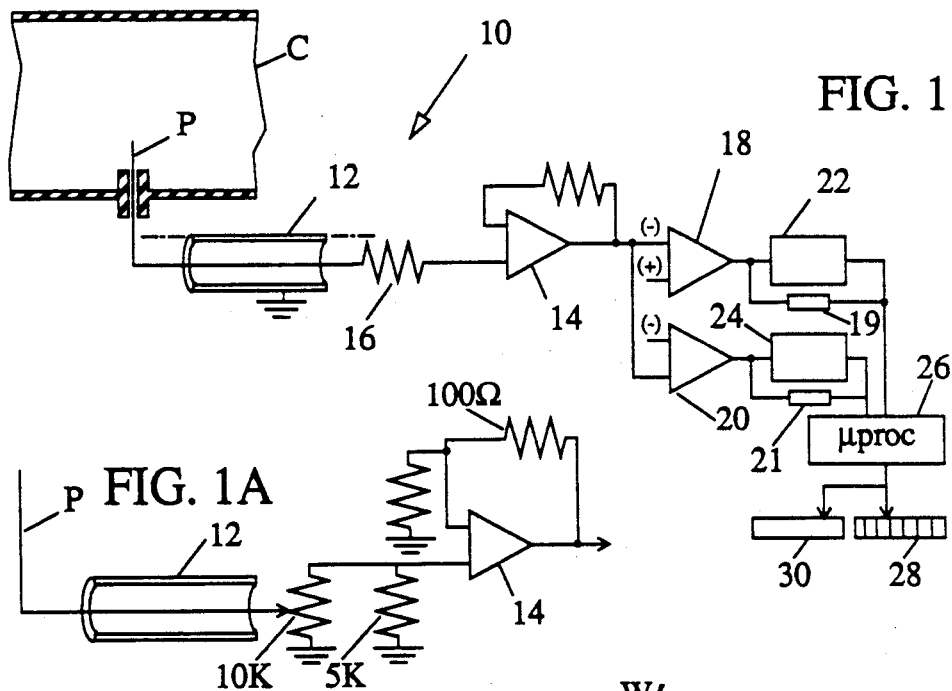
FIG. 1
FIG. 1A
FIG. 1B
FIG. 2A
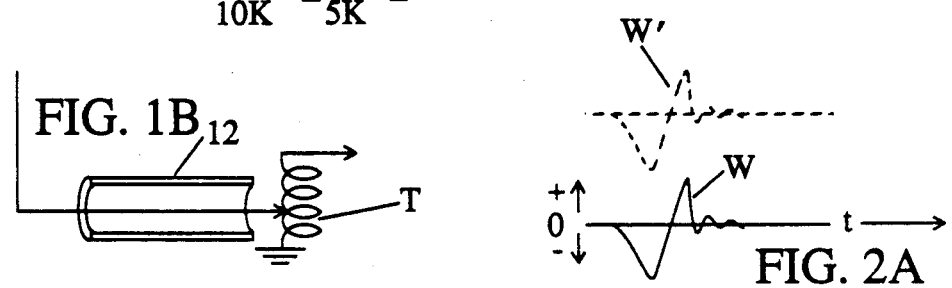
FIG. 2
FIG. 2B
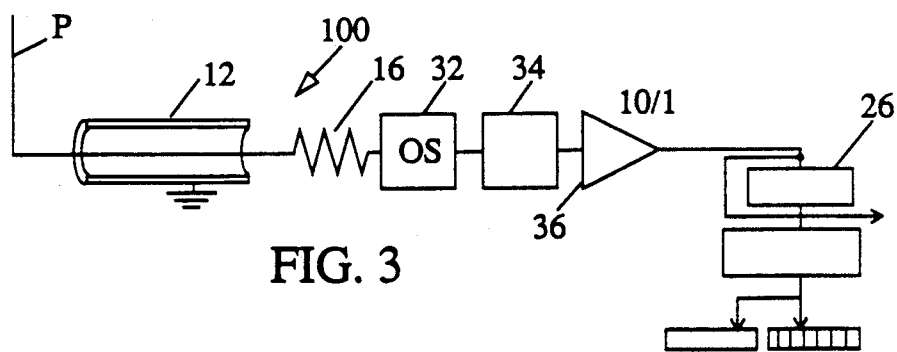
FIG. 3

FLOW MEASUREMENT BY COLLISION CHARACTERIZATION

BACKGROUND OF THE INVENTION

The present invention relates to flow measurement and more particularly to measurement of fluid flows with suspended solid particles, an area of measurement now served by triboelectric instruments. These comprise probes or rings in or around the flowstream coupled to a high gain current amplifier and measuring means. The triboelectric interactions with the probe generate currents on the order of $10^{-10}$ to $10^{-14}$ amperes.

Some triboelectric systems can be vulnerable to confusion engendered by probe contamination, battery effects, noise problems of the instrument and/or the flow system measured, long averaging times to factor out noise effects and/or the high impedance of the feedback resistors associated with their high current gain amplifiers. The high impedance aggravates probe contamination vulnerability. Measured triboelectric currents are integrals of charge transfer,—a phenomenon occuring at uncertain rates in many industrial systems to be measured.

It is the object of the present invention to provide an electrical (non-optical, non-radioactive, non-magnetic or Hall Effect based) flow measuring system which can be used for characterization of a flow of suspended solid particles in a flow (liquid or gas)—i.e., characterization of the flow velocity, mass flow particle concentration and/or relative proportions of mixed particle species, in a manner overcoming one or more, preferably all, of the above problems.

SUMMARY OF THE INVENTION

The invention comprises a collision analysis system which has a probe, of wire or ring or other form, in or adjacent to the flow to be measured, an amplifier of high bandwith and fast response characteristic (or no amplifier at all, as to certain industrial applications, for ultimate high bandwidth and fast response); a comparator/counter system; and an output. The system literally reponds to single particle collisions with the probe (or other related single particle interaction, e.g., a near miss which has an electrical response analogous to response to a collision) on the probe. The collision events (or the like) take place in times of $10^{-8}$-$10^{-6}$ seconds. The measurement of such events is free of d.c. components (unlike conventional triboelectric systems).

Preferably, each such even can be captured as an electrical pulse and multiple pulses can be counted. But other forms of analysis of such events can be implemented within the scope of the invention.

Feedback impedances of a single-particle -collision- analysis count instrument are orders of magnitude lower than for traditional instruments and traditional concerns arising from probe contamination are avovided. Complexities of quantizing electrons per hit are also avoided.

Others objects, features, and advantages will be apparent from the following detailed descriptionof preferred embodiments taken in conjunction with the accompanying drawing in which:

BRIEF DESCRIPTION OF THE DRAWING

FIGS. 1 and 3 are schematics of a collision analysis system in accordance with a preferred embodiment of the invention;

FIGS. 1A and 1B are schematics of variants of portions of the FIG. 1 system;

FIGS. 2 and 2A are voltage pulse representations of responses engendered in the FIG. 1 apparatus;

FIG. 2B is a sketch of a probe/particle interaction (of the FIG. 1 apparatus) on a special case defined below; and FIG. 3 is a schematic of another embodiment of the system, usable in certain applications without the high gain amplifier of the FIG. 1 system.

DETAILED DESCRIPTION OF PREFERRED EMBODIMENTS

FIG. 1 shows a tubular flow conduit C with a triboelectric probe P of rod or wire form (or annular ring electrode embedded in the wall or a screen electrode). The probe is connected via a coaxial cable 12 to an instrument 10 comprising a wide band high gain amplifier 14 with feedback to a summing junction ($\Sigma$). A small value resistor 16 (of 10-100 ohms) is inserted in series between the coaxial line and the amplifier to protect the amplifier. The voltage gain of the amplifier is on the order of 10-1000 for large particles and considerable higher for small particles.

The amplifier gain bandwidth product is preferably in the Gigahertz bandwidth range to effectively isolate charge transfer events (collision of a particle with the probe or other triboelectric interaction).

The system senses an alternating current from the electrode with a nanosecond order of magnitude wavelength pulse ($1 \times 10^{31\ 8} - 1 \times 10^{-10}$ seconds) and a 1-10 Gigahertz gain-bandwidth product amplification.

Plus charge event and minus charge event (in excess of (+) and (−) thresholds) operational amplifier comparators 18 and 20, typically of IM311 type for low collision rate situations, are provided together with counters 22 and 24 to provide an absolute total (as well as (+) and (−) sub-totals) of charge transfer events to a microprocessor 26. Signal processors 19 and 21 (including AD converters) are also provided for allowing direct processor access to digitized representations of each charge transfer event, for further useful information content. The microprocessor can be connected to the usual display elements 28, records, or process controllers 30.

Where the conduit comprises an environment of moving, suspended particles with significant precharge, the amplifier 14 can be derated as to gain—or even eliminated in favor of essentaily direct connection of the input line to the comparator/counter apparatus. Examples of such pre-charge situations include electrostatic precipitator devices. We have learned that an electron transfer rate occurs upon a particle in such a device hitting a triboelectric probe, in excess of $10^{10}$ electrons per impact. Intrinsically conductive particles (e.g., metal, carbon powders, conductive ceramics, specialty aluminas and conductive plastics) behave similarly. Such a high level of precharge or conductivity allows elemination of the amplifier. The typical charge transfer rates for non-charged, insulating particles are in the $10^4$-$10^7$ electrons per impact range, with full charge transfer usually taking place in 0.1 to 10.0 microseconds; i.e. the precharged particles effectg 3 -6 orders of magnitude increase in charge transfer compared to insulating particles.

FIGS. 1A and 1B show variants of the front end including use of a non-inverting feedback and/or a transformer T for noiseless gain.

FIG. 2 shows a voltage-time trace of sequential detected pulses with (+) and (−) spikes in sequence, various threshhold levels ($T_1$, $T_2$, $T_3$, $T_4$). The apparatus can be sensitized for counting pulses of different amplitude ranges. FIG. 2A shows an expanded view of one type of pulse response wherein a single insulating particle's (M) interaction with a conductive probe P shown in FIG. 2B with a path P1 pre-impact and an orbital/spinning path P2 post-impact with spin S (due to localization of charge transfer at a zone M (on the particle's surface) yields a wave form W' or W normalized as to zero axis with a post-impact ringing response.

FIG. 3 shows an instrumentation circuit 100, for use with pre-charged particle collisions, similar to that of FIG. 1 but lacking the high gain amplifier and including a one-shot pulse trigger 32 (non-standard width, narrow imput pulse standard width output pulse), an integrating (averaging) circuit 34, a 100× gain amplifier 36, connected directly to the microprocessor 26 or directly to output devices.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. Method of flow measurement of fluids carrying suspended solid particles comprising the steps of:
   (a) inducing collisions of individual ones of the solid particles with charge transfer means,
   (b) measuring each such collision of a solid particle with the charge transfer means by sensing an alternating current from the electrode with a nanosecond order of magnitude wavelength pulse ($1 \times 10^{-8}$–$1 \times 10^{-10}$ seconds) and a 1–10 Giaghertz gain - bandwidth product amplification.

2. Apparatus for flow measurement of fluids carrying suspended solid particles comprising:
   (a) means for intercepting a portion of the solid particles with charge transfer means,
   (b) means for measuring each such collisions of a solid particle with the charge transfer means by pulse counting via: sensing an alternating current from the electrode with a nanosecond order of magnitude wavelength pulse ($1 \times 10^{-8}$–$1 \times 10^{-10}$ seconds) and a 1–10 Gigahertz gain - bandwidth product amplifier.

3. Apparatus in accordance with claim 2 comprising multiple devices for measuring charge transfers of different polarity as induced by said collisions and means for summing the outputs of the multiple devices.

4. Apparatus in accordance with claim 3 wherein the devices are operational amplifier comparators counting charge transfers above a threshold.

* * * * *